(12) United States Patent
Govari

(10) Patent No.: US 7,974,680 B2
(45) Date of Patent: Jul. 5, 2011

(54) HYSTERESIS ASSESSMENT FOR METAL IMMUNITY

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 1095 days.

(21) Appl. No.: 10/448,289

(22) Filed: May 29, 2003

(65) Prior Publication Data

US 2004/0239314 A1 Dec. 2, 2004

(51) Int. Cl.
*A61B 5/05* (2006.01)

(52) U.S. Cl. .................. 600/424; 606/130; 324/207.12

(58) Field of Classification Search .................. 600/424, 600/407; 606/130; 324/207.12; 702/94
See application file for complete search history.

(56) References Cited

U.S. PATENT DOCUMENTS

| | | | |
|---|---|---|---|
| 3,644,825 A | 2/1972 | Davis, Jr. et al. .............. 324/41 |
| 3,868,565 A | 2/1975 | Kuipers ..................... 324/34 R |
| 4,017,858 A | 4/1977 | Kuipers ..................... 343/100 R |
| 4,054,881 A | 10/1977 | Raab ......................... 343/112 R |
| 4,173,228 A | 11/1979 | Van Steenwyk et al. | |
| 4,287,809 A | 9/1981 | Egli et al. ..................... 89/41 EA |
| 4,309,697 A | 1/1982 | Weaver | |
| 4,317,078 A | 2/1982 | Weed et al. ................... 324/208 |
| 4,416,289 A | 11/1983 | Bresler ......................... 128/737 |
| 4,526,177 A | 7/1985 | Rudy et al. ..................... 128/737 |
| 4,560,930 A | 12/1985 | Kouno ........................... 324/207 |
| 4,605,897 A | 8/1986 | Gelinas | |
| 4,613,866 A | 9/1986 | Blood ............................ 343/448 |
| 4,622,542 A | 11/1986 | Weaver | |
| 4,642,786 A | 2/1987 | Hansen ......................... 364/559 |
| 4,651,436 A | 3/1987 | Gaal .............................. 33/533 |
| 4,710,708 A | 12/1987 | Rorden et al. ................. 324/207 |
| 4,771,237 A | 9/1988 | Daley | |
| 4,791,412 A | 12/1988 | Brooks | |
| 4,849,692 A | 7/1989 | Blood | |
| 4,868,504 A | 9/1989 | Johnson | |
| 4,905,698 A | 3/1990 | Strohl, Jr. et al. | |

(Continued)

FOREIGN PATENT DOCUMENTS

EP 0964261 A2 5/1999

(Continued)

OTHER PUBLICATIONS

Feiste, K.L. et al. Characterization of Nodular Cast Iron Properties by Harmonic Analysis of Eddy Current Signals, ECNDT98, Oct. 1998, vol. 3, No. 10.

(Continued)

*Primary Examiner* — Sanjay Cattungal
(74) *Attorney, Agent, or Firm* — Louis J. Capezzuto

(57) ABSTRACT

Assessment apparatus is provided, including a set of one or more radiators, which is adapted to generate an energy field at at least one fundamental frequency. A receiving sensor is adapted to generate a first signal responsive to the energy field when an interfering article is at a first location relative to the receiving sensor, and is adapted to generate a second signal responsive to the energy field when the interfering article is at a second location relative to the receiving sensor. A control unit is adapted to (a) receive and analyze the first and second signals, in order to compute a fingerprint signal characteristic of the interfering article, and (b) store, in a database, data indicative of the fingerprint signal, in association with an identity of the interfering article.

25 Claims, 3 Drawing Sheets

U.S. PATENT DOCUMENTS

| | | | |
|---|---|---|---|
| 4,931,730 A | 6/1990 | Olsen et al. | |
| 4,945,305 A | 7/1990 | Blood | |
| 5,002,137 A | 3/1991 | Dickinson et al. | 175/19 |
| 5,008,649 A | 4/1991 | Klein | |
| 5,028,869 A | 7/1991 | Dobmann et al. | |
| 5,042,486 A | 8/1991 | Pfeiler et al. | 128/653 R |
| 5,057,095 A | 10/1991 | Fabian | |
| 5,068,608 A | 11/1991 | Clark, Jr. | 324/220 |
| 5,099,845 A | 3/1992 | Besz et al. | |
| 5,172,056 A | 12/1992 | Voisin | 324/207.17 |
| 5,211,165 A | 5/1993 | Dumoulin et al. | 128/653.1 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,265,610 A | 11/1993 | Darrow et al. | 128/653.1 |
| 5,269,289 A | 12/1993 | Takehana et al. | 128/4 |
| 5,273,025 A | 12/1993 | Sakiyama et al. | 128/6 |
| 5,274,328 A | 12/1993 | Begin et al. | |
| 5,309,913 A | 5/1994 | Kormos et al. | 128/653.1 |
| 5,325,873 A | 7/1994 | Hirschi et al. | |
| 5,375,596 A | 12/1994 | Twiss et al. | 128/653.1 |
| 5,377,678 A | 1/1995 | Dumoulin et al. | 128/653.1 |
| 5,391,199 A | 2/1995 | Ben-Haim | |
| 5,425,367 A | 6/1995 | Shapiro et al. | |
| 5,425,382 A | 6/1995 | Golden et al. | |
| 5,429,132 A | 7/1995 | Guy et al. | 128/653.1 |
| 5,437,277 A | 8/1995 | Dumoulin et al. | 128/653.1 |
| 5,443,489 A | 8/1995 | Ben-Haim | |
| 5,453,687 A | 9/1995 | Zierdt et al. | 324/207.17 |
| 5,506,506 A | 4/1996 | Candy | |
| 5,519,317 A | 5/1996 | Guichard et al. | |
| 5,534,873 A | 7/1996 | Weichman et al. | |
| 5,553,611 A | 9/1996 | Budd et al. | |
| 5,558,091 A | 9/1996 | Acker et al. | |
| 5,577,502 A | 11/1996 | Darrow et al. | 128/653.1 |
| 5,600,330 A | 2/1997 | Blood | |
| 5,622,169 A | 4/1997 | Golden et al. | 128/653.1 |
| 5,629,621 A | 5/1997 | Goldfine et al. | |
| 5,633,711 A | 5/1997 | Nelson et al. | |
| 5,644,229 A | 7/1997 | Dossel et al. | |
| 5,646,524 A | 7/1997 | Gilboa | 234/207.17 |
| 5,682,886 A | 11/1997 | Delp et al. | 128/653.1 |
| 5,694,945 A | 12/1997 | Ben-Haim | 128/736 |
| 5,715,822 A | 2/1998 | Watkins et al. | 128/653.5 |
| 5,729,129 A * | 3/1998 | Acker | 324/207.12 |
| 5,752,513 A | 5/1998 | Acker et al. | 128/653.1 |
| 5,767,669 A * | 6/1998 | Hansen et al. | 324/207.12 |
| 5,769,843 A | 6/1998 | Abela et al. | 606/10 |
| 5,797,849 A | 8/1998 | Vesely et al. | 600/461 |
| 5,831,260 A | 11/1998 | Hansen | |
| 5,847,976 A | 12/1998 | Lescourret | |
| 5,879,297 A | 3/1999 | Haynor et al. | 600/407 |
| 5,899,860 A | 5/1999 | Pfeiffer et al. | |
| 5,913,820 A | 6/1999 | Bladen et al. | |
| 5,967,980 A * | 10/1999 | Ferre et al. | 600/424 |
| 5,997,473 A | 12/1999 | Taniguchi et al. | 600/117 |
| 6,073,043 A * | 6/2000 | Schneider | 600/424 |
| 6,122,538 A | 9/2000 | Silwa, Jr. et al. | |
| 6,127,821 A | 10/2000 | Ramsden et al. | |
| 6,147,480 A | 11/2000 | Osadchy et al. | |
| 6,150,810 A | 11/2000 | Roybal | |
| 6,172,499 B1 * | 1/2001 | Ashe | 324/207.12 |
| 6,177,792 B1 | 1/2001 | Govari et al. | |
| 6,201,987 B1 | 3/2001 | Dumoulin | |
| 6,226,547 B1 | 5/2001 | Lockhart et al. | |
| 6,239,724 B1 | 5/2001 | Doron et al. | |
| 6,246,231 B1 | 6/2001 | Ashe | |
| 6,246,898 B1 * | 6/2001 | Vesely et al. | 600/424 |
| 6,366,799 B1 * | 4/2002 | Acker et al. | 600/424 |
| 6,369,564 B1 | 4/2002 | Khalfin et al. | |
| 6,373,240 B1 | 4/2002 | Govari | |
| 6,373,387 B1 | 4/2002 | Qiu et al. | |
| 6,400,139 B1 * | 6/2002 | Khalfin et al. | 324/207.17 |
| 6,427,079 B1 | 7/2002 | Schneider et al. | |
| 6,443,894 B1 | 9/2002 | Sumanaweera et al. | |
| 6,484,049 B1 | 11/2002 | Seeley et al. | |
| 6,484,118 B1 | 11/2002 | Govari | |
| 6,493,573 B1 | 12/2002 | Martinelli et al. | |
| 6,690,963 B2 * | 2/2004 | Ben-Haim et al. | 600/424 |
| 6,774,624 B2 * | 8/2004 | Anderson et al. | 324/207.17 |
| 6,788,967 B2 * | 9/2004 | Ben-Haim et al. | 600/424 |
| 2001/0035815 A1 | 11/2001 | Fletcher et al. | |
| 2002/0065455 A1 * | 5/2002 | Ben-Haim et al. | 600/407 |
| 2002/0165448 A1 * | 11/2002 | Ben-Haim et al. | 600/424 |

FOREIGN PATENT DOCUMENTS

| | | |
|---|---|---|
| FR | 763861 | 5/1934 |
| JP | 10094609 | 4/1998 |
| WO | WO 92/03090 | 3/1992 |
| WO | WO 94/04938 | 3/1994 |
| WO | WO 94/23647 | 10/1994 |
| WO | WO 96/05768 | 2/1996 |
| WO | WO 96/41119 | 12/1996 |
| WO | WO 97/29678 | 8/1997 |
| WO | WO 97/29679 | 8/1997 |
| WO | WO 97/29709 | 8/1997 |
| WO | WO 97/29710 | 8/1997 |
| WO | WO 97/32179 | 9/1997 |
| WO | WO 97/42517 | 11/1997 |
| WO | WO 98/36236 | 8/1998 |
| WO | WO 99/32033 | 7/1999 |
| WO | WO 99/52430 | 10/1999 |

OTHER PUBLICATIONS

John David Jackson, "Classical Electrodynamics", Second Edition, John Wiley & Sons, New York, 1975, p. 178.

William H. Press et al., "Numerical Recipes in C, The Art of Scientific Computing", Second Edition, Cambridge University Press, ISBN 052143108, pp. 383-393.

Pending U.S. Appl. No. 09/621,322, filed Jul. 20, 2000, Biosense, Inc.

Pending U.S. Appl. No. 10/302,112, Biosense, Inc.

Pending U.S. Appl. No. 10/448,291, Biosense, Inc.

European Search Report dated Oct. 10, 2001.

European Search Report EP 04253229 dated Sep. 21, 2004.

\* cited by examiner

HYSTERESIS ASSESSMENT FOR METAL IMMUNITY

CROSS-REFERENCES TO RELATED APPLICATIONS

This application is related to U.S. Pat. No. 7,433,728 filed on even date, entitled, "Dynamic metal immunity by hysteresis," which is assigned to the assignee of the present patent application and is incorporated herein by reference.

FIELD OF THE INVENTION

The present invention relates generally to non-contact tracking of objects using a magnetic field, and specifically to counteracting the effect of a moving, magnetic field-responsive article in a magnetic field.

BACKGROUND OF THE INVENTION

Non-contact electromagnetic locating and tracking systems are well known in the art, with an exceptionally broad spectrum of applications, including such diverse topics as military target sighting, computer animation, and precise medical procedures. For example, electromagnetic locating technology is widely used in the medical field during surgical, diagnostic, therapeutic and prophylactic procedures that entail insertion and movement of objects such as surgical devices, probes, and catheters within the body of the patient. The need exists for providing real-time information for accurately determining the location and orientation of objects within the patient's body, preferably without using X-ray imaging.

U.S. Pat. Nos. 5,391,199 and 5,443,489 to Ben-Haim, which are assigned to the assignee of the present patent application and whose disclosures are incorporated herein by reference, describe systems wherein the coordinates of an intrabody probe are determined using one or more field sensors, such as Hall effect devices, coils, or other antennae carried on the probe. Such systems are used for generating three-dimensional location information regarding a medical probe or catheter. A sensor coil is placed in the catheter and generates signals in response to externally-applied magnetic fields. The magnetic fields are generated by a plurality of radiator coils, fixed to an external reference frame in known, mutually-spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

PCT Patent Publication WO 96/05768 to Ben-Haim et al., which is assigned to the assignee of the present patent application and whose disclosure is incorporated herein by reference, describes a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates, so that the position and orientation of the catheter are known without the need for imaging the catheter.

U.S. Pat. No. 6,239,724 to Doron et al., whose disclosure is incorporated herein by reference, describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

U.S. Pat. No. 5,425,382 to Golden, et al., whose disclosure is incorporated herein by reference, describes apparatus and methods for locating a catheter in the body of a patient by sensing the static magnetic field strength gradient generated by a magnet fixed to the catheter.

U.S. Pat. No. 5,558,091 to Acker et al., which is assigned to the assignee of the present patent application and whose disclosure is incorporated herein by reference, describes a magnetic position and orientation determining system which uses uniform fields from Helmholtz coils positioned on opposite sides of a sensing volume and gradient fields generated by the same coils. By monitoring field components detected at a probe during application of these fields, the position and orientation of the probe is deduced. A representation of the probe is superposed on a separately-acquired image of the subject to show the position and orientation of the probe with respect to the subject.

Other locating devices using a position sensor attached to a catheter are described in U.S. Pat. No. 4,173,228 to Van Steenwyk et al., U.S. Pat. No. 5,099,845 to Besz et al., U.S. Pat. No. 5,325,873 to Hirschi et al., U.S. Pat. No. 5,913,820 to Bladen et al., U.S. Pat. No. 4,905,698 to Strohl, Jr. et al., and U.S. Pat. No. 5,425,367 to Shapiro et al., the disclosures of which are incorporated herein by reference.

Commercial electrophysiological and physical mapping systems based on detecting the position of a probe inside the body are presently available. Among them, CARTO™, developed and marketed by Biosense Webster, Inc. (Diamond Bar, Calif.), is a system for automatic association and mapping of local electrical activity with catheter location.

Electromagnetic locating and tracking systems are susceptible to inaccuracies when a metal or other magnetically-responsive article is introduced into the vicinity of the object being tracked. Such inaccuracies occur because the magnetic fields generated in this vicinity by the location system's radiator coils are distorted. For example, the radiator coils' magnetic fields may generate eddy currents in such an article, and the eddy currents then cause parasitic magnetic fields that react with the field that gave rise to them. In a surgical environment, for example, there is a substantial amount of conductive and permeable material including basic and ancillary equipment (operating tables, carts, movable lamps, etc.) as well as invasive surgery apparatus (scalpels, catheters, scissors, etc.). The eddy currents generated in these articles and the resultant electromagnetic field distortions can lead to errors in determining the position of the object being tracked.

It is known to address the problem of the interference of static metal objects by performing an initial calibration, in which the response of the system to a probe placed at a relatively large number of points of interest is measured. This may be acceptable for addressing stationary sources of electromagnetic interference, but it is not satisfactory for solving the interference problems induced by moving magnetically-responsive objects.

U.S. Pat. No. 6,373,240 to Govari, entitled, "Counteracting metal presence in a magnetic tracking system," which is assigned to the assignee of the present patent application and is incorporated herein by reference, describes an object tracking system comprising one or more sensor coils adjacent to a locatable point on an object being tracked, and one or more radiator coils, which generate alternating magnetic fields in a vicinity of the object when driven by respective alternating electrical currents. For each radiator coil, a frequency of its alternating electrical current is scanned through a plurality of values so that, at any specific time, each of the radiator coils radiates at a frequency which is different from the frequencies at which the other radiator coils are radiating.

The sensor coils generate electrical signals responsive to the magnetic fields, which signals are received by signal processing circuitry and analyzed by a computer or other processor. When a metal or other field-responsive article is in the vicinity of the object, the signals typically include position signal components responsive to the magnetic fields generated by the radiator coils at their respective instantaneous driving frequencies, and parasitic signal components responsive to parasitic magnetic fields generated because of the article. The parasitic components are typically equal in frequency to the instantaneous frequency of the driving frequency, but are shifted in phase, so that the effect at each sensor coil is to produce a combined signal having a phase and an amplitude which are shifted relative to the signal when no field-responsive article is present. The phase-shift is a function of the driving frequency, and so will vary as each driving frequency is scanned. The computer processes the combined signal to find which frequency produces a minimum phase-shift, and thus a minimum effect of the parasitic components, and this frequency is used to calculate the position of the object. Varying the driving frequency until the phase shift is a minimum is described as an effective method for reducing the effect of field-responsive articles on the signal.

U.S. Pat. No. 6,172,499 to Ashe, whose disclosure is incorporated herein by reference, describes a device for measuring the location and orientation in the six degrees of freedom of a receiving antenna with respect to a transmitting antenna utilizing multiple-frequency AC magnetic signals. The transmitting component consists of two or more transmitting antennae of known location and orientation relative to one another. The transmitting antennae are driven simultaneously by AC excitation, with each antenna occupying one or more unique positions in the frequency spectrum. The receiving antennae measure the transmitted AC magnetic field plus distortions caused by conductive metals. As described, a computer then extracts the distortion component and removes it from the received signals, providing the correct position and orientation output.

U.S. Pat. No. 6,246,231 to Ashe, whose disclosure is incorporated herein by reference, describes a method of flux containment in which the magnetic fields from transmitting elements are confined and redirected from the areas where conducting objects are commonly found.

U.S. Pat. No. 5,767,669 to Hansen et al., whose disclosure is incorporated herein by reference, describes a method for subtracting eddy current distortions produced in a magnetic tracking system. The system utilizes pulsed magnetic fields from a plurality of generators, and the presence of eddy currents is detected by measuring rates of change of currents generated in sensor coils used for tracking. The eddy currents are compensated for by adjusting the duration of the magnetic pulses.

U.S. Pat. Nos. 4,945,305 and 4,849,692 to Blood, whose disclosures are incorporated herein by reference, describe tracking systems that circumvent the problems of eddy currents by using pulsed DC magnetic fields. Sensors which are able to detect DC fields are used in the systems, and eddy currents are detected and adjusted for by utilizing the decay characteristics and the amplitudes of the eddy currents.

U.S. Pat. No. 5,600,330 to Blood, whose disclosure is incorporated herein by reference, describes a non-dipole loop transmitter-based magnetic tracking system. This system is described as showing reduced sensitivity to small metallic objects in the operating volume.

European Patent Application EP 0-964,261 A2 to Dumoulin, whose disclosure is incorporated herein by reference, describes systems for compensating for eddy currents in a tracking system using alternating magnetic field generators. In a first system the eddy currents are compensated for by first calibrating the system when it is free from eddy currents, and then modifying the fields generated when the eddy currents are detected. In a second system the eddy currents are nullified by using one or more shielding coils placed near the generators.

U.S. Pat. No. 5,831,260 to Hansen, whose disclosure is incorporated herein by reference, describes a combined electromagnetic and optical hybrid locating system that is intended to reduce the disadvantages of each individual system operating alone.

U.S. Pat. No. 6,122,538 to Sliwa, Jr. et al., whose disclosure is incorporated herein by reference, describes hybrid position and orientation systems using different types of sensors including ultrasound, magnetic, tilt, gyroscopic, and accelerometer subsystems for tracking medical imaging devices.

Article surveillance systems using soft magnetic materials and low frequency detection systems have been known since the Picard patent (Ser. No. 763,861), which is incorporated herein by reference, was issued in France in 1934. Surveillance systems based on this approach generally use a marker consisting of ferromagnetic material having a high magnetic permeability. When the marker is interrogated by a magnetic field generated by the surveillance system, the marker generates harmonics of the interrogating frequency because of the non-linear hysteresis loop of the material of the marker. The surveillance system detects, filters, and analyzes these harmonics in order to determine the presence of the marker. Numerous patents describe systems based on this approach and improvements thereto, including, for example, U.S. Pat. Nos. 4,622,542 and 4,309,697 to Weaver, U.S. Pat. No. 5,008,649 to Klein, and U.S. Pat. No. 6,373,387 to Qiu et al., the disclosures of which are incorporated herein by reference.

U.S. Pat. No. 4,791,412 to Brooks, whose disclosure is incorporated herein by reference, describes an article surveillance system based upon generation and detection of phase shifted harmonic signals from encoded magnetic markers. The system is described as incorporating a signal processing technique for reducing the effects of large metal objects in the surveillance zone.

U.S. Pat. No. 6,150,810 to Roybal, U.S. Pat. No. 6,127,821 to Ramsden et al., U.S. Pat. No. 5,519,317 to Guichard et al., and U.S. Pat. No. 5,506,506 to Candy, the disclosures of which are incorporated herein by reference, describe apparatus for detecting the presence of ferrous objects by generating a magnetic field and detecting the response to the field from the object. A typical application of such an apparatus is detection and discrimination of objects buried in the ground. U.S. Pat. No. 4,868,504 to Johnson, whose disclosure is incorporated herein by reference, describes a metal detector for locating and distinguishing between different classes of metal objects. This apparatus performs its analysis by using harmonic frequency components of the response from the object.

U.S. Pat. No. 5,028,869 to Dobmann et al., whose disclosure is incorporated herein by reference, describes apparatus for the nondestructive measurement of magnetic properties of a test body by detecting a tangential magnetic field and deriving harmonic components thereof. By analyzing the harmonic components, the apparatus calculates the maximum pitch of the hysteresis curve of the test body.

An article by Feiste K L et al. entitled, "Characterization of Nodular Cast Iron Properties by Harmonic Analysis of Eddy Current Signals," NDT.net, Vol. 3, No. 10 (1998), available as of May 2002 at http://www.ndt.net/article/ecndt98/nuclear/245/245.htm, which is incorporated herein by reference, describes applying harmonic analysis to nodular cast iron samples to evaluate the technique's performance in predicting metallurgical and mechanical properties of the samples.

There is a need for a straightforward, accurate, real-time method that addresses the problem of interference induced in electromagnetic locating and tracking systems caused by the introduction of non-stationary metallic or other magnetically-responsive articles into the measurement environment.

SUMMARY OF THE INVENTION

It is an object of some aspects of the present invention to provide apparatus and methods for improving the accuracy of electromagnetic locating and tracking systems.

It is also an object of some aspects of the present invention to provide apparatus and methods for increasing accuracy of electromagnetic location and tracking systems without concern for the presence of moving electrically- and/or magnetically-responsive materials in the space wherein measurements are being taken.

It is a further object of some aspects of the present invention to provide apparatus and methods for enabling electromagnetic location and tracking systems to function accurately in the presence of moving electrically- and/or magnetically-responsive materials in the space wherein the measurements are being taken, substantially without regard to the quantity of such materials, their conductive characteristics, velocities, orientation, direction and the length of time that such materials are within the space.

It is yet a further object of some aspects of the present invention to provide apparatus and methods for operating electromagnetic location and tracking systems without the necessity of employing means for reducing or circumventing the effects caused by eddy currents induced in moving electrically- and/or magnetically-responsive objects in the space wherein measurements are being taken.

In preferred embodiments of the present invention, apparatus for electromagnetic locating and tracking of an object, such as a probe, in a space, such as a body of a patient, comprises a plurality of electromagnetic radiators located in the vicinity of the space, a position sensor, fixed to the probe, and a control unit adapted to drive the radiators and process signals from the position sensor. To enable sensing of the position of the probe, one or more fundamental frequencies are transmitted by the radiators. When a magnetic field-responsive element, for example a surgical tool, movable lamp, cart, etc., is introduced into the vicinity of the probe, the measured position of the probe differs from its absolute position. To compensate for this interference effect on the probe, the absolute position of the probe is calculated by using a harmonic correction algorithm.

Correction is possible by use of such an algorithm because the signal received by the probe includes not only the transmitted fundamental signal but also one or more higher harmonics of the fundamental frequency, caused, for example, by phase shifting due to the non-linearity of the interfering element's hysteresis loop or caused by other factors. The pattern of these harmonics is analyzed by the control unit and compared to a previously-generated database of patterns associated with specific types of elements, in order to determine the type of element that is causing interference. The interfering effect of the element is then calculated, responsive to the type of element and the magnitude of the harmonics, and removed, such as by subtraction, from the signal received by the probe. The resulting clean signal is used as an input for calculating the absolute position of the probe.

Advantageously, in these embodiments of the present invention it is generally not necessary to employ means to reduce or circumvent the effects caused by eddy currents induced in non-stationary magnetic field-responsive elements in the space. Further advantageously, these embodiments of the present invention typically achieve the objective of accurate tracking regardless of the number of metal elements introduced to the surrounding space, their conductive characteristics, velocities, orientation, direction and the length of time that the elements are within the space.

In some preferred embodiments of the present invention, prior to apparatus being used with a patient, each element that may interfere with measurements of the position of the probe is assessed, in order to "train" the apparatus that will be used with the patient as to the interfering effect of a given element. To assess each element, the radiators generate fundamental frequencies which are measured by a receiving coil twice: first, not in the presence of the element, and second, in the presence of the element. In the presence of the element, the signal received is distorted by interference from the element. Each type of material generally has a unique hysteresis curve and therefore generates different interference and corresponding different higher harmonics. For each radiated fundamental frequency, the control unit preferably removes the clean received signal from the distorted received signal. The resulting signal, representing the effect of the element's interference on the clean signal, is generally unique for each element and therefore serves as a "fingerprint" of the element. To reduce the effect of noise and other random variations in measurement, this calculation process may be repeated with the element in different locations, and the results combined, such as by averaging, in order to generate the fingerprint. Data indicative of the fingerprint, such as a pattern of the fingerprint, is stored in association with the identity of the assessed article in a database.

Alternatively, in some preferred embodiments of the present invention, to assess each element, the radiators generate fundamental frequencies which are measured by a receiving coil twice: first, with the element at a first location, and second, with the element at a second location. The distortion of a first signal received when the element is at the first location differs from the distortion of a second signal received when the element is at the second location. For each radiated fundamental frequency, the control unit preferably calculates the difference between the first and second signals, such as by subtraction. The resulting signal, representing the effect of the element's interference on a signal that would have been received in the absence of the element, is generally unique for each element and therefore serves as a fingerprint of the element. To reduce the effect of noise and other random variations in measurement, measurements may be made when the element is in more than two locations, and the results of the calculation combined, such as by averaging, in order to generate the fingerprint. Data indicative of each fingerprint, such as a pattern of the fingerprint, is stored in association with the identity of the assessed article in a database.

In some preferred embodiments, the assessment procedure is performed in a location other than an operating room environment. For example, the assessment procedure is performed in a different location in the medical facility in which the procedure is to be performed. After assessment, the resulting assessment data and calculations are transferred to the control unit.

Alternatively or additionally, assessment is performed offsite, preferably by a third party. In this case, preferably a large number of elements and/or materials commonly used in performing medical procedures are assessed. These assessments are stored as a library in a repository, such as a database. This library is transferred to the control unit, either before or after the control unit is delivered to its user, or, alternatively, the library is transferred to a computer system or network to which the control unit has access during a procedure. It will be appreciated that onsite and offsite assessment can easily be combined, giving the user of the system the ability to add interfering elements not included in the available library or libraries.

In some preferred embodiments of the present invention, the control unit is coupled to the probe and radiators by leads. Alternatively, the probe comprises circuitry which transmits wireless signals responsive to electromagnetic radiation generated by the radiators.

It is noted that whereas some embodiments of the present invention are described with respect to assessing the element by placing the element at two different locations and maintaining the receiving coil at a generally fixed location, this is by way of illustration and not limitation. The scope of the present invention includes assessing the element by placing the element at a generally fixed location and having the receiving coil measure the field when the receiving coil is at respective first and second locations. Alternatively or additionally, both the receiving coil and the element are moved during the assessment. Each of these assessment options is an example of changing the relative positions of the receiving coil and the element.

For some applications, apparatus and method described herein are adapted to work in conjunction with apparatus and methods described in U.S. Pat. No. 7,809,421, entitled, "Medical system calibration with static metal compensation," and/or in U.S. Pat. No. 7,433,728, entitled, "Dynamic metal immunity," which are assigned to the assignee of the present patent application and are incorporated herein by reference.

There is therefore provided, in accordance with an embodiment of the present invention, apparatus for tracking an object in a body of a patient in the presence of an interfering article, including:

a set of one or more radiators, which are adapted to generate an energy field at a fundamental frequency in a vicinity of the object;

a position sensor, fixed to the object, which is adapted to generate a signal responsive to the energy field; and a control unit, with access to a database of one or more harmonic frequency patterns associated with one or more respective specific types of interfering articles, the control unit adapted to:

receive the signal, detect a pattern of harmonic frequencies of the fundamental frequency present in the signal responsive to an interaction of the interfering article with the energy field, compare the pattern to harmonic frequency patterns stored in the database, identify the interfering article responsive to the comparison, correct the signal responsive to the identification of the interfering article and a magnitude of one or more of the harmonic frequencies in the detected pattern, and determine position coordinates of the object responsive to the corrected signal.

Typically, the interfering article is ferromagnetic, and the control unit is adapted to identify the ferromagnetic interfering article.

In an embodiment, the position sensor includes at least one of: a Hall effect device, a coil, and an antenna.

The fundamental frequency is typically between about 200 Hz and about 12 kHz, and the radiators are adapted to generate the energy field at the fundamental frequency.

For some applications, the control unit is adapted to detect the pattern of harmonic frequencies by calculating a ratio of an amplitude of a first harmonic of the fundamental frequency present in the signal to an amplitude of a second harmonic of the fundamental frequency present in the signal, and to compare the pattern to harmonic frequency patterns stored in the database by comparing the calculated ratio to ratios stored in the database.

In an embodiment, the control unit is adapted to correct the signal by calculating an interfering effect of the interfering article on the signal, and by removing the interfering effect from the signal. For example, the control unit may be adapted to remove the interfering effect by subtracting, in a frequency domain, the interfering effect from the signal.

Alternatively or additionally, the control unit is adapted to calculate the interfering effect by:

calculating a ratio of an amplitude of at least one of the harmonic frequencies of the fundamental frequency present in the signal to an amplitude of the fundamental frequency present in the signal, and comparing the calculated ratio to ratios stored in the database.

There is further provided, in accordance with an embodiment of the present invention, tracking apparatus, including:

an object, adapted to be inserted in a body of a patient;

a set of one or more radiators, which are adapted to generate an energy field at a fundamental frequency in a vicinity of the object;

a position sensor, fixed to the object, which is adapted to generate a signal responsive to the energy field; and a control unit, with access to a database of one or more harmonic frequency patterns associated with one or more respective specific types of interfering articles, the control unit adapted to:

receive the signal, detect a pattern of harmonic frequencies of the fundamental frequency present in the signal responsive to an interaction of an article with the energy field, compare the pattern to harmonic frequency patterns stored in the database, identify the article responsive to the comparison, correct the signal responsive to the identification of the article and a magnitude of one or more of the harmonic frequencies in the detected pattern, and determine position coordinates of the object responsive to the corrected signal.

There is still further provided, in accordance with an embodiment of the present invention, apparatus for tracking an object in a body of a patient, including: a set of one or more radiators, fixed to the object, which radiators are adapted to generate an energy field at a fundamental frequency;

a set of one or more position sensors, located in a vicinity of the object, which are adapted to generate respective signals responsive to the energy field; and a control unit, with access to a database of one or more harmonic frequency patterns associated with one or more respective specific types of interfering articles, the control unit adapted to:
   receive the signal,
   detect a pattern of harmonic frequencies of the fundamental frequency present in the signal responsive to an interaction of an article with the energy field,
   compare the pattern to harmonic frequency patterns stored in the database,
   identify the article responsive to the comparison,
   correct the signal responsive to the identification of the article and a magnitude of one or more of the harmonic frequencies in the detected pattern, and
   determine position coordinates of the object responsive to the corrected signal.

There is yet further provided, in accordance with an embodiment of the present invention, a method for tracking an object in a body of a patient in the presence an interfering article, including:
generating an energy field at a fundamental frequency;
receiving a signal generated responsive to the energy field;
detecting a pattern of harmonic frequencies of the fundamental frequency present in the signal responsive to an interaction of the interfering article with the energy field;
comparing the pattern to harmonic frequency patterns stored in a database of one or more patterns associated with one or more respective specific types of interfering articles;
identifying the interfering article responsive to the comparison;
correcting the signal responsive to the identification of the interfering article and a magnitude of one or more of the harmonic frequencies in the detected pattern; and
determining position coordinates of the object responsive to the corrected signal.

There is also provided, in accordance with an embodiment of the present invention, a computer software product for tracking an object in a body of a patient in the presence of an interfering article, the product including a computer-readable medium, in which program instructions are stored, which instructions, when read by a computer, cause the computer to:
receive a signal generated by a sensor exposed to an energy field at a fundamental frequency;
   detect a pattern of harmonic frequencies of the fundamental frequency present in the signal responsive to an interaction of the interfering article with the energy field;
compare the pattern to harmonic frequency patterns stored in a database of one or more patterns associated with one or more respective specific types of interfering articles;
identify the interfering article responsive to the comparison;
correct the signal responsive to the identification of the interfering article and a magnitude of one or more of the harmonic frequencies in the detected pattern; and
determine position coordinates of the object responsive to the corrected signal.

The present invention will be more fully understood from the following detailed description of preferred embodiments thereof, taken together with the drawings, in which:

DETAILED DESCRIPTION OF PREFERRED EMBODIMENTS

Figure 1:
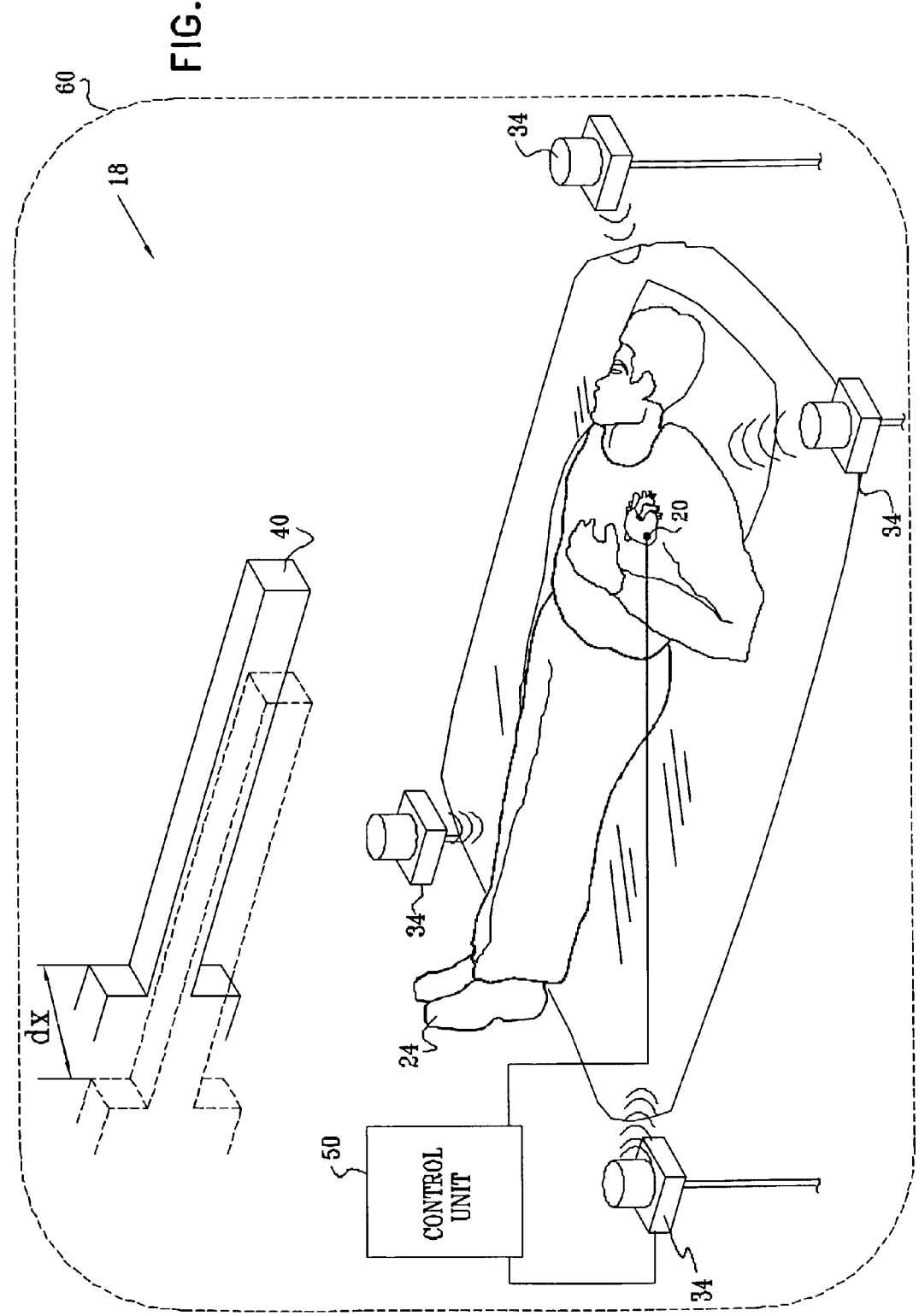
FIG. 1 is a schematic, pictorial illustration of an electromagnetic locating and tracking system used during a medical procedure, in accordance with a preferred embodiment of the present invention.

FIG. 1 is a schematic, pictorial illustration of an electromagnetic locating and tracking system 18 utilized to track an object, such as a probe 20, in the body of a patient 24 while providing immunity to the introduction, movement (dx), or removal of an interfering element 40, such as a ferromagnetic element, in or near a space 60 around the patient, in accordance with a preferred embodiment of the present invention. System 18 comprises a set of radiators 34, which are driven by a control unit 50 to track probe 20, preferably but not necessarily using methods and apparatus which are described in the above-cited US Patents and PCT Patent Publication to Ben-Haim and Ben-Haim et al. Thus, probe 20 comprises a position sensor (not shown), which preferably comprises field sensors, such as Hall effect devices, coils, or other antennae, for use in position determination. Alternatively or additionally, methods and apparatus known in the art are used to facilitate the tracking of probe 20. Control unit 50 comprises circuitry for processing signals received from probe 20, for detecting element 40, and for calculating the absolute position of probe 20 using a harmonic correction algorithm, as described hereinbelow.

Element 40 typically comprises an article made completely or partially of magnetically permeable material, such as ferromagnetic material. Examples of such articles include surgical tools, movable lamps, and carts. Element 40 generates parasitic fields, the phases and amplitudes of which generally depend on properties of element 40, including its dielectric constant, magnetic permeability, geometrical shape and orientation relative to probe 20. It will be appreciated that although element 40 is shown in FIG. 1 as a single element, element 40 could comprise a number of separate elements, which are often brought in and out of the area of a medical procedure.

Figure 2:
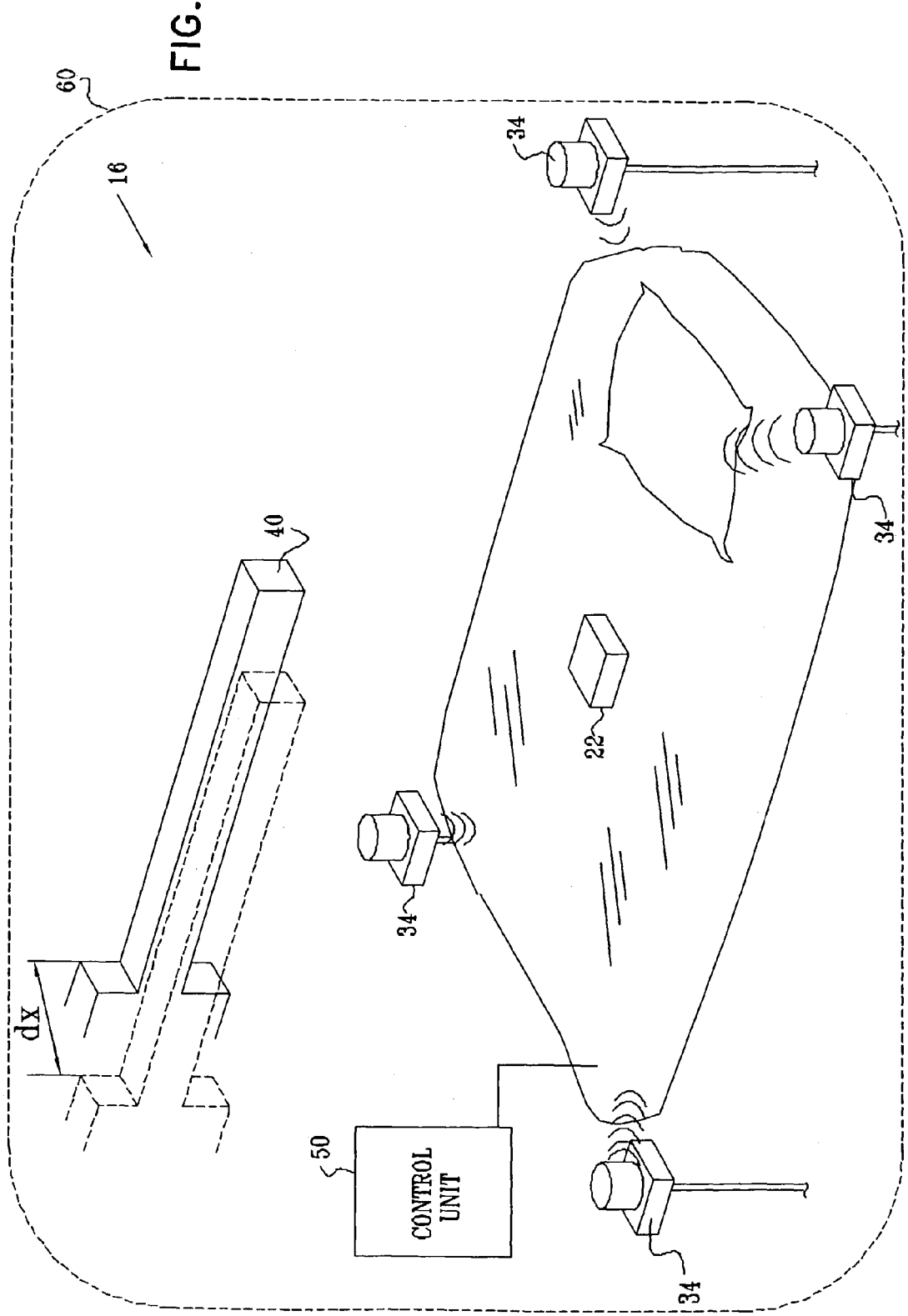
FIG. 2 is a schematic, pictorial illustration of an assessment system, in accordance with a preferred embodiment of the present invention.

FIG. 2 is a schematic, pictorial illustration of an assessment system 16, in accordance with a preferred embodiment of the present invention. In this preferred embodiment, prior to system 18 being used on a patient, each element 40 which may interfere with measurements of the position of probe 20 is preferably assessed by assessment system 16. To assess each element 40, the element is initially not present in space 60. One or more radiators 34 radiate a fundamental frequency for which assessment is desired. Alternatively, radiators 34 radiate a plurality of fundamental frequencies for which assessment is desired, one frequency at a time. Suitable frequencies are typically between about 200 Hz and about 12 kHz. The one or more fundamental frequencies radiated are preferably those used by radiators 34 for position sensing of probe 20 during a procedure. A receiving coil 22, fixed at any point in space 60, receives the radiated signals and conveys them to control unit 50. In a preferred embodiment of the present invention, receiving coil 22 comprises a sensor, such as a coil, Hall effect device or other antenna, dedicated to this function. In this case, the sensor in receiving coil 22 preferably is substantially identical to the sensor in probe 20. Alternatively, probe 20, temporarily fixed at any point in space 60, functions as receiving coil 22. Further alternatively, one of radiators 34, which is not being used for radiating during assessment, functions as receiving coil 22. For some applications, receiving coil 22 is oriented so that at least one of its sensors (such as a coil) is oriented to increase or maximize the strength of the signal received.

In the next step of the assessment process, element 40 is introduced into space 60, preferably near receiving coil 22. Each of the one or more fundamental frequencies radiated before the introduction of element 40 is again radiated by the same radiators 34. Receiving coil 22 receives the radiated signals and conveys them to control unit 50. In the case of a ferromagnetic element, the signal received is distorted by interference caused in part by phase shifting caused by the non-linearity of the element's hysteresis loop. This non-linearity of the hysteresis loop also induces higher harmonics of the radiated fundamental frequency. Each type of material generally has a unique hysteresis curve and therefore generates different interference and a corresponding different pattern of higher harmonics.

Figure 3A:
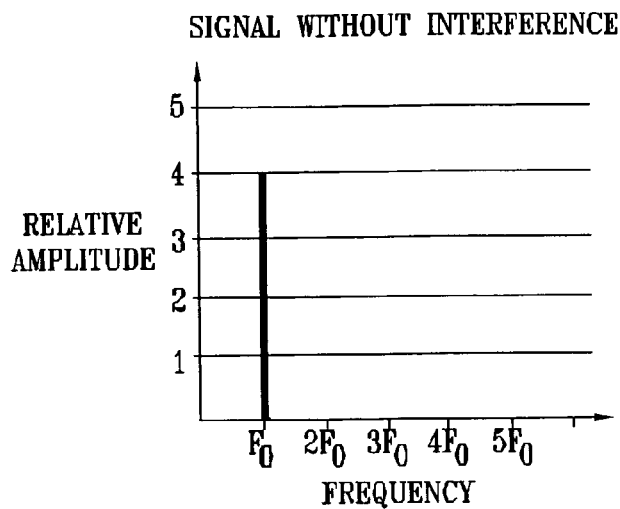
FIGS. 3A, 3B, and 3C are simplified frequency response graphs illustrating an example assessment of an interfering element, in accordance with a preferred embodiment of the present invention.
Figure 3B:
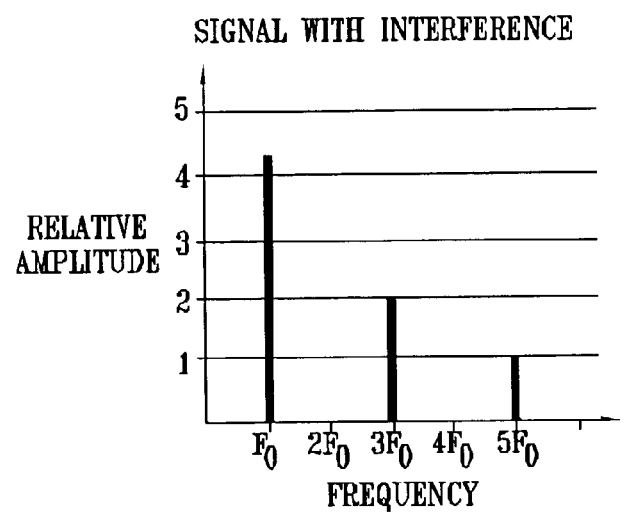
Figure 3C:
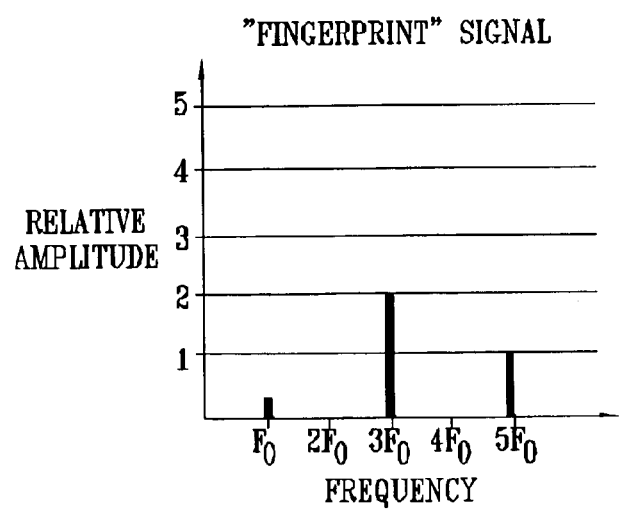

Reference is now made to FIGS. 3A, 3B, and 3C, which show, for a single radiated fundamental frequency, a simplified example of received signals and a calculated "fingerprint," in accordance with a preferred embodiment of the present invention. FIG. 3A shows the signal received by receiving coil 22 prior to the introduction of element 40 in space 60 (the "clean received signal"), the amplitudes of which at $F_0$, $3F_0$, and $5F_0$ are 4.0, 0.0, and 0.0, respectively. FIG. 3B shows the signal received by receiving coil 22 after the introduction of element 40 in space 60 (the "distorted received signal"), the amplitudes of which at $F_0$, $3F_0$, and $5F_0$ are 4.3, 2.0, and 1.0, respectively. For each radiated fundamental frequency, control unit 40 analyzes the received signals, preferably by removing the clean received signal from the distorted received signal, such as by subtraction. The resulting signal, shown in FIG. 3C, represents the effect of electromagnetic interference of element 40 on the clean received signal. In this example, this "fingerprint" signal has amplitudes at $F_0$, $3F_0$, and $5F_0$ of 0.3, 2.0, and 1.0, respectively. Each type of material generally causes a unique resulting subtracted signal, which allows these signals to serve as fingerprint signals. It will be understood that the harmonic frequencies shown in FIGS. 3B and 3C are illustrative only; in practice, among other differences, higher harmonics generally are present. As described hereinbelow, the ratios of the amplitudes at the different frequencies, rather than the absolute values of the amplitudes, are typically stored and used for correction during position determination.

Alternatively, in a preferred embodiments of the present invention, to assess each element, radiators 34 generate fundamental frequencies which are measured by a receiving coil 22 twice: first, with element 40 at a first location in space 60, and second, with element 40 at a second location in space 60. The distortion of a first signal received when the element is at the first location differs from the distortion of a second signal received when the element is at the second location. For each radiated fundamental frequency, control unit 50 preferably calculates the difference between the first and second signals, such as by subtraction. The resulting signal (or ratios of its amplitudes at different frequencies, as described hereinbelow), representing the effect of the interference of element 40 on a signal that would have been received in the absence of element 40, is generally unique for each element 40 and therefore serves as a fingerprint of the element. To reduce the effect of noise and other random variations in measurement, measurements may be made when the element is in more than two locations, and the results of the calculation averaged in order to generate the fingerprint.

For example, assume that the signal shown in FIG. 3B represents the first signal generated when element 40 is at the first location (as mentioned above, the amplitudes of this signal at $F_0$, $3F_0$, and $5F_0$ are 4.3, 2.0, and 1.0, respectively). Further assume that the amplitudes of the second signal (not shown) at $F_0$, $3F_0$, and $5F_0$, generated when element 40 is at the second location, are 4.6, 4.0, and 2.0, respectively. Subtracting the first signal from the second signal results in a fingerprint signal with amplitudes at $F_0$, $3F_0$, and $5F_0$ of 0.3, 2.0, and 1.0, respectively. Ratios of these values are stored and used for correction during a procedure, as described hereinbelow. Substantially the same ratios typically result even when measurements are made at multiple first and second locations.

The table below illustrates examples of three fingerprint signals (with arbitrary example values), in accordance with a preferred embodiment of the present invention. Element #1 represents the example element reflected in FIGS. 3A, 3B, and 3C, and elements #2 and #3 represent two other example elements. Reference is made to the left portion of the table, labeled "Frequency." $f_o$ represents the transmitted fundamental frequency, the multiples of $f_O$ represent harmonic frequencies thereof, and the values represent relative amplitudes.

| | Frequency | | | | | Ratio | |
|---|---|---|---|---|---|---|---|
| | $f_0$ | $2f_0$ | $3f_0$ | $4f_0$ | $5f_0$ | $5f_0/3f_0$ | $3f_0/f_0$ |
| Element #1 | 0.2 | — | 2.0 | — | 1.0 | 0.5 | 10.0 |
| Element #2 | 0.3 | — | 1.5 | — | 1.2 | 0.8 | 5.0 |
| Element #3 | 0.1 | — | 1.0 | — | 0.6 | 0.6 | 10.0 |

Reference is now made to the right portion of the table, labeled "Ratio." In a preferred embodiment of the present invention, for each element for which assessment is performed, ratios between two or more harmonic frequencies, and between one or more harmonic frequencies and the transmitted fundamental frequency ($f_o$) are calculated, preferably by control unit 50 or, alternatively, by an external computer system (not shown). Each individual element assessed is uniquely characterized by its calculated ratio and/or ratios. Other possible algorithms, e.g., using combinations of two or more harmonic frequencies with the transmitted fundamental frequency and/or with each other, will be apparent to those skilled in the art having read the disclosure of the present patent application. Such other algorithms may be performed in order to produce alternative or additional values that uniquely identify different types of elements. Alternatively or additionally, assessment ratios and/or other calculated results are obtained for specific types of materials rather than specific types of elements. (Identifying the specific interfering material, without necessarily identifying the object comprising the material, is generally sufficient to perform the correction techniques described herein.) These ratios and/or results of other calculations are preferably stored in a database to which control unit 50 has access, and are used during a procedure for position compensation calculations, as described hereinbelow. ("Database," as used in the specification and in the claims, is to be understood as including substantially any suitable repository, memory device or data structure that may be used for storing this information.)

In a preferred embodiment, the assessment procedure is performed in a location other than an operating room environment. For example, the assessment procedure is performed in a different location in the medical facility in which the procedure is to be performed. In this embodiment, preferably one or more radiators substantially identical to radiators 34 are provided. After assessment, the resulting assessment data and calculations are transferred to control unit 50 using methods obvious to those skilled in the art.

Alternatively or additionally, assessment is performed offsite, preferably by a third party. In this case, preferably a large number of elements and/or materials commonly used in performing medical procedures are assessed. These assessments are stored as a library in a repository, such as a database. (It is to be understood that substantially any suitable memory device and data structure may be used for storing the library.) This library is transferred to control unit 50, either before or after control unit 50 is delivered to its user, using methods known in the art. Alternatively, the library is transferred to a computer system or network to which control unit 50 has access during a procedure. It will be appreciated that onsite and offsite assessment can easily be combined, giving the user of system 18 the ability to add elements 40 not included in the available library or libraries. Other details of implementing such a library system will be evident to those skilled in the art, having read the disclosure of the present patent application.

Reference is again made to FIG. 1. During a procedure being performed on a patient, when element 40 is introduced into the vicinity of space 60, the measured position of probe 20 differs from its actual position because of the interference generated by element 40. In a preferred embodiment of the present invention, to compensate for this interference, the harmonics induced in the signal received by probe 20 are analyzed by control unit 50. Calculations are performed on the amplitudes of the harmonics, such as the determination of ratios between the amplitudes of two or more harmonics. The results of these calculations are compared with those stored in the memory of control unit 50 in order to identify the type of previously-assessed element and/or material that element 40 is or includes, respectively. Once the element and/or material is known, the distorting effect of element 40 on the amplitude of the fundamental signal of interest received by probe 20 is calculated, for example by using the ratio of the amplitude of one or more of the harmonics to the amplitude of the fundamental signal, as calculated during the assessment and stored in a database to which control unit 50 has real-time access. The amplitude of this distorting effect is subtracted from the measured amplitude of the received fundamental signal of interest. The remaining signal, no longer distorted by the presence of element 40, is used as an input by control unit 50 for calculating the absolute position of probe 20.

Reference is again made to the right portion of the table above, labeled "Ratio," in order to provide an example of the calculation of an interference correction, using simple ratios of two harmonics, in accordance with a preferred embodiment of the present invention. For example, assume that, in the signal received by probe 20, the relative amplitude of $f_o$ is 4.1, the relative amplitude of $3f_o$ is 1.0, and the relative amplitude of $5f_o$ is 0.5. The ratio of $5f_o$ to $3f_o$ is therefore 0.5. By comparing this ratio to the stored values reflected in the table, control unit 50 determines that, in this case, element 40 is the same type as element #1. To determine the distorting effect of element 40 on the received signal, the value of $3f_o$ (1.0) is divided by the stored ratio of $3f_o/f_o$ (10.0), resulting in 0.1. This result is subtracted from the measured amplitude of $f_o$ (4.1), resulting in a corrected amplitude of 4.0, which is no longer distorted by the presence of element #1. This amplitude is used as an input for calculating the accurate position of probe 20.

In a preferred embodiment of the present invention, only one harmonic frequency is used to determine the identity of element 40. This is possible, for example, when one or more elements 40 being used during a procedure produce very different relative amplitudes at a certain harmonic frequency.

In a preferred embodiment of the present invention, during procedures in which multiple elements 40 are introduced into space 60 during a procedure, control unit 50 identifies each element 40 individually by performing suitable calculations. In some cases, these calculations use a number of higher harmonics, which provide additional distinguishing characteristics for elements 40, in order to aid in distinguishing multiple elements 40.

In a preferred embodiment of the present invention, when two or more elements 40 are made of the same ferromagnetic material or combination of ferromagnetic materials, there is generally no need to distinguish between these elements during a procedure. The interfering effect of such elements is combined and uniquely identifiable by the fingerprint of their material. Detection of and corrections for such elements is therefore preferably performed as a group by system 18, substantially without modification to the procedures described hereinabove.

Preferred embodiments of the present invention have been described with respect to a location system 18 wherein radiators 34 transmit electromagnetic signals and probe 20 receives these signals. It is to be understood that the scope of the present invention includes application of the techniques described herein to location systems wherein the probe transmits electromagnetic signals and radiators receive these signals.

It is to be understood that preferred embodiments of the present invention are described herein with respect to invasive medical techniques by way of example only. The scope of the present invention includes application of the techniques described herein to electromagnetic locating and tracking systems used for any purpose whatsoever.

It is to be further understood that the techniques described herein are applicable to assessment, identification and compensation for particular elements, e.g., a particular tool of known composition, as well as to assessment, identification and compensation for particular materials, e.g., a common ferromagnetic material. An "interfering article," as used in the specification and the claims, is thus to be understood as including both a particular discrete element (such as a tool) or a particular material (such as steel). Techniques described specifically with respect to element 40, element 41, or any other interfering article may be interchanged, as appropriate. It is still further to be understood that control unit 50 may comprise a general-purpose computer, which is programmed in software to carry out the functions described herein. The software may be downloaded to the computer in electronic form, over a network, for example, or it may alternatively be supplied to the computer on tangible media, such as a CD-ROM. Further alternatively, control unit 50 may be implemented in dedicated hardware logic, or using a combination of hardware and software elements.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Assessment apparatus for determining a fingerprint signal of an interfering article in an energy field for a medical procedure, comprising:

a set of one or more radiators, which is adapted to generate an energy field at at least one fundamental frequency;

a receiving sensor, which is adapted to generate a first signal responsive to the energy field when an interfering article is at a first location relative to the receiving sensor, the first location being in a vicinity of the receiving sensor, the first signal defining a distorted signal, the receiving sensor being adapted to generate a second signal responsive to the energy field when the interfering article is at a second location relative to the receiving sensor, the second location not being in a vicinity of the receiving sensor such that the interfering article has substantially no effect on the second signal, the second signal defining a clean signal; and a control unit, which is adapted to:
receive a first amplitude of the first signal and a second amplitude of the second signal from the receiving sensor,
subtract the second amplitude of the second signal from the first amplitude of the first signal, in order to compute a fingerprint signal characteristic of the interfering article based on the clean signal and the distorted signal, and
store, in a database, data indicative of the fingerprint signal, in association with an identity of the interfering article.

2. Apparatus according to claim 1, wherein the interfering article is ferromagnetic, and wherein the receiving sensor is adapted to generate the first and second signals when the ferromagnetic interfering article is at the first and second locations, respectively.

3. Apparatus according to claim 1, wherein the receiving sensor comprises at least one of: a Hall effect device, a coil, and an antenna.

4. Apparatus according to claim 1, wherein the fundamental frequency is between about 200 Hz and about 12 kHz, and wherein the radiators are adapted to generate the energy field at the fundamental frequency.

5. Apparatus according to claim 1,
wherein the at least one fundamental frequency comprises a plurality of fundamental frequencies, wherein the set of radiators is adapted to generate a plurality of energy fields at the plurality of fundamental frequencies,
wherein the receiving sensor is adapted to generate first and second signals responsive to each of the plurality of energy fields, and
wherein the control unit is adapted to compute fingerprint signals for the first and second signals at each of the fundamental frequencies, and to store in the database respective data indicative of the fingerprint signals, in association with the identity of the interfering article and in association with the respective fundamental frequency.

6. Apparatus according to claim 1, wherein the control unit is adapted to calculate a ratio of an amplitude of at least one harmonic frequency of the fundamental frequency present in the fingerprint signal to an amplitude of the fundamental frequency present in the fingerprint signal, and to store the ratio, in the database, in association with the identity of the interfering article.

7. Apparatus according to claim 1, wherein the first signal is acquired from more than two first locations and the control unit calculates an average of the more than two first locations in order to generate the first signal.

8. Apparatus according to claim 1, wherein the data indicative of the fingerprint signal includes a harmonic frequency pattern of the fundamental frequency present in the fingerprint signal, and wherein the control unit is adapted to detect the pattern, and to store the pattern in the database in association with the identity of the interfering article.

9. Apparatus according to claim 8, wherein the control unit is adapted to detect the harmonic frequency pattern by calculating a ratio of an amplitude of a first harmonic of the fundamental frequency in the fingerprint signal to an amplitude of a second harmonic of the fundamental frequency in the fingerprint signal, and to store the pattern in the database in association with the identity of the interfering article.

10. A method for determining a fingerprint signal of an interfering article in an energy field for a medical procedure, comprising:
generating an energy field at at least one fundamental frequency;
generating a first signal at a receiving sensor responsive to the energy field when an interfering article is at a first location relative to a site of the receiving sensor, the first location being in the vicinity of the receiving sensor, the first signal defining a distorted signal;
generating a second signal at the receiving sensor responsive to the energy field when the interfering article is at a second location relative to a site of the receiving sensor, the second location not being in the vicinity of the receiving sensor such that the interfering article has substantially no effect on the second signal, the second signal defining a clean signal;
receiving a first amplitude of the first signal and a second amplitude of the second signal;
subtracting the second amplitude of the second signal from the first amplitude of the first signal, so as to compute a fingerprint signal characteristic of the article based on the clean signal and the distorted signal; and
storing, in a database, data indicative of the fingerprint signal, in association with an identity of the interfering article.

11. A method according to claim 10,
wherein the interfering article is ferromagnetic,
wherein generating the first signal comprises generating the first signal when the ferromagnetic interfering article is at the first location, and
wherein generating the second signal comprises generating the second signal when the ferromagnetic interfering article is at the second location.

12. A method according to claim 10, wherein the fundamental frequency is between about 200 Hz and about 12 kHz, and wherein generating the energy field comprises generating the energy field at the fundamental frequency.

13. A method according to claim 10,
wherein the at least one fundamental frequency comprises a plurality of fundamental frequencies,
wherein generating the energy field comprises generating a plurality of energy fields at the respective plurality of fundamental frequencies,
wherein generating the first and second signals comprises generating respective first and second signals responsive to each of the plurality of energy fields,
wherein analyzing the first and second signals comprises computing fingerprint signals for the first and second signals at each of the fundamental frequencies, and
wherein storing the data comprises storing in the database respective data indicative of the fingerprint signals, in association with the identity of the interfering article and in association with the respective fundamental frequency.

14. A method according to claim 10, wherein storing the harmonic frequency pattern comprises calculating a ratio of an amplitude of at least one harmonic frequency of the fundamental frequency present in the fingerprint signal to an amplitude of the fundamental frequency present in the fingerprint signal, and storing the ratio, in the database, in association with an identity of the interfering article.

15. A method according to claim 10, wherein the first signal is generated from an average of more than two first locations.

16. A method according to claim 10, wherein storing the data comprises detecting a harmonic frequency pattern of the fundamental frequency present in the fingerprint signal, and storing the pattern in the database in association with the identity of the interfering article.

17. A method according to claim 16, wherein detecting the harmonic frequency pattern comprises calculating a ratio of an amplitude of a first harmonic of the fundamental frequency to an amplitude of a second harmonic of the fundamental frequency, and wherein storing the pattern comprises storing the ratio.

18. A computer software product for determining a fingerprint signal of an interfering article in an energy field for a medical procedure, the product comprising a computer-readable storage device, in which program instructions are stored, which instructions, when read by a computer, cause the computer to:
receive a first signal generated by a sensor when exposed to an energy field at at least one fundamental frequency when an interfering article is at a first location relative to a site of the sensor, the first location being in the vicinity of the sensor, the first signal defining a distorted signal;
receive a second signal generated by the sensor when exposed to the energy field when the interfering article is at a second location relative to a site of the sensor, the second location not being in the vicinity of the sensor such that the interfering article has substantially no effect on the second signal, the second signal defining a clean signal;
receive a first amplitude of the first signal and a second amplitude of the second signal;
subtract the second amplitude of the second signal from the first amplitude of the first signal, so as to compute a fingerprint signal characteristic of the article based on the clean signal and the distorted signal; and
store, in a database, data indicative of the fingerprint signal, in association with an identity of the interfering article.

19. A product according to claim 18,
wherein the interfering article is ferromagnetic, and
wherein the instructions cause the computer to receive the first signal generated when the ferromagnetic interfering article is at the first location, and to receive the second signal generated when the ferromagnetic interfering article is at the second location.

20. A product according to claim 18, wherein the fundamental frequency is between about 200 Hz and about 12 kHz, and wherein the instructions cause the computer to receive the first and second signals generated by the sensor when exposed to the energy field.

21. A product according to claim 18,
wherein the at least one fundamental frequency includes a plurality of fundamental frequencies, and
wherein the instructions cause the computer to:
receive respective first and second signals generated by the sensor when exposed to a plurality of energy fields at the plurality of fundamental frequencies, and
analyze the first and second signals, so as to compute fingerprint signals for the first and second signals at each of the fundamental frequencies, and to store in the database respective data indicative of the fingerprint signals, in association with the identity of the interfering article and in association with the respective fundamental frequency.

22. A product according to claim 18, wherein the instructions cause the computer to calculate a ratio of an amplitude of at least one of the harmonic frequencies of the fundamental frequency present in the fingerprint signal to an amplitude of the fundamental frequency present in the fingerprint signal, and to store the ratio in the database in association with the identity of the interfering article.

23. A product according to claim 18, wherein the first signal is generated from an average of more than two first locations.

24. A product according to claim 18, wherein the instructions cause the computer to detect a harmonic frequency pattern of the fundamental frequency present in the fingerprint signal, and to store the pattern in the database in association with the identity of the interfering article.

25. A product according to claim 24, wherein the instructions cause the computer to detect the harmonic frequency pattern by calculating a ratio of an amplitude of a first harmonic of the fundamental frequency to an amplitude of a second harmonic of the fundamental frequency, and to store the ratio in the database in association with the identity of the interfering article.

* * * * *